United States Patent
Pearson et al.

(10) Patent No.: US 8,980,792 B2
(45) Date of Patent: Mar. 17, 2015

(54) COMPOSITIONS COMPRISING ABSCISIC ACID AND A FUNGICIDALLY ACTIVE COMPOUND

(75) Inventors: Elizabeth Pearson, Basel (CH); Jose Luis Calvo, Bracknell (GB); Robin Wesley, Bracknell (GB); Jeremy R. Godwin, Stein (CH); Ryan Jon Langs Ramsey, Reading (GB); Timothy Robert Hawkes, Bracknell (GB)

(73) Assignees: Syngenta Participations AG, Basel (CH); Syngenta Limited, Surrey (GB)

( * ) Notice: Subject to any disclaimer, the term of this patent is extended or adjusted under 35 U.S.C. 154(b) by 53 days.

(21) Appl. No.: 13/880,616

(22) PCT Filed: Oct. 21, 2011

(86) PCT No.: PCT/EP2011/068438
§ 371 (c)(1), (2), (4) Date: Jul. 8, 2013

(87) PCT Pub. No.: WO2012/052547
PCT Pub. Date: Apr. 26, 2012

(65) Prior Publication Data
US 2013/0274307 A1    Oct. 17, 2013

(30) Foreign Application Priority Data
Oct. 21, 2010 (EP) .................................. 10188312

(51) Int. Cl.
*A01N 25/00* (2006.01)
*A01N 39/02* (2006.01)
*A01N 43/56* (2006.01)
*A61K 31/415* (2006.01)
*A01N 37/42* (2006.01)

(52) U.S. Cl.
CPC ................ *A01N 25/00* (2013.01); *A01N 37/42* (2013.01)
USPC ........ 504/100; 504/116.1; 504/145; 514/406; 424/405

(58) Field of Classification Search
CPC ........ A01N 25/00; A01N 43/56; A01N 35/06
See application file for complete search history.

(56) References Cited

U.S. PATENT DOCUMENTS
2010/0324101 A1*  12/2010  Ebbinghaus et al. ......... 514/355

FOREIGN PATENT DOCUMENTS
| WO | 2007/008580 | 1/2007 |
| WO | 2010/015337 | 2/2010 |
| WO | 2010/086103 | 8/2010 |
| WO | 2010/136139 | 12/2010 |

OTHER PUBLICATIONS
International Search Report, International Application No. PCT/EP2011/068438, completion date: May 9, 2012.

* cited by examiner

*Primary Examiner* — Alton Pryor
(74) *Attorney, Agent, or Firm* — James Cueva

(57) ABSTRACT

The present invention relates to methods comprising applying to a useful plant, the locus thereof or propagation material thereof a combination of abscisic acid and a fungicidally active compound, which fungicidally active compound is a succinate dehydrogenase inhibitor, in particular for increasing the potency of a fungicidally active compound. The invention also relates to compositions comprising abscisic acid and the fungicidally active compounds as well as seeds comprising the combinations.

8 Claims, No Drawings

COMPOSITIONS COMPRISING ABSCISIC ACID AND A FUNGICIDALLY ACTIVE COMPOUND

This application is a 371 of International Application No. PCT/EP2011/068438 filed Oct. 21, 2011, which claims priority to EP 10188312.2 filed Oct. 21,2010, the contents of which are incorporated herein by reference.

The present invention relates to combinations of abscisic acid and a fungicidally active compound, which fungicidally active compound is a succinate dehydrogenase inhibitor. In particular, the invention relates to methods of applying the combinations to plants, as well as compositions and seeds comprising the combinations.

The class of fungicides known as succinate dehydrogenase inhibitors is an art-recognised class with a mode of action that targets the enzyme succinate dehydrogenase (SDH, so-called complex II in the mitochondrial respiration chain), which is a functional part of the tricarboxylic cycle and linked to the mitochondrial electron transport chain. Examples include Isopyrazam, Sedaxane, Penthiopyrad, Bixafen and Fluxapyroxad.

Abscisic acid (ABA) is also known as abscisin II and dormin. It has the formula S—(Z,E)]-5-(1-Hydroxy-2,6,6-trimethyl-4-oxo-2-cyclohexen-1-yl)-3-methyl-2,4-pentanedienoic acid:

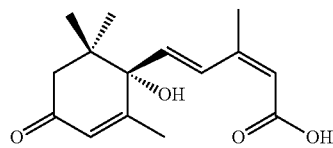

Abscisic acid is known to play a role in how plants respond to weather stresses such as cold and drought. WO 2007/008580 describes methods of imparting increased stress resistance on a plant, in particular increasing plant drought and cold resistance, by application of abscisic acid and one or more specific triazole compounds. WO 2010/015337 describes the use of specific azoles for increasing the resistance of plants to abiotic stress factors.

There is a continuing need to find methods of protecting plants from phytopathogenic organisms, whilst limiting the impact of such methods on the environment.

It has now surprisingly been found that abscisic acid can increase the fungicidal effect of fungicides from the class of succinate dehydrogenase inhibitors. This allows the rate of application of the fungicides to be reduced whilst maintaining a high level of efficacy.

Accordingly, in a first aspect the invention provides a method comprising applying to a useful plant, the locus thereof or propagation material thereof a combination of abscisic acid and a fungicidally active compound, which fungicidally active compound is a succinate dehydrogenase inhibitor. The method may be for increasing the potency of the fungicidally active compound. Increasing the potency, means for example, increasing the fungicidal effect using the same amount of fungicidal compound.

In a further aspect the invention provides a method of increasing the potency of a fungicidally active compound, which fungicidally active compound is a succinate dehydrogenase inhibitor, comprising applying abscisic acid to a useful plant, the locus thereof or propagation material thereof.

The method may also comprise applying the succinate dehydrogenase inhibitor to the useful plant, the locus thereof or propagation material thereof.

In a further aspect the invention provides a method comprising mixing abscisic acid and a fungicidally active compound, which fungicidally active compound is a succinate dehydrogenase inhibitor. Said mixing may be to produce a composition comprising the abscisic acid and succinate dehydrogenase inhibitor prior to application to a useful plant, the locus thereof or propagation material thereof. Alternatively, said mixing may occur in situ by applying the abscisic acid and succinate dehydrogenase inhibitor separately to a useful plant, the locus thereof or propagation material thereof.

In a further aspect the invention provides a composition comprising abscisic acid and a fungicidally active compound, which fungicidally active compound is a succinate dehydrogenase inhibitor. The composition may additionally comprise customary formulation ingredients, e.g. a carrier, surfactant, optionally an adjuvant. The composition may also comprise additional active ingredients, e.g. insecticide, a fungicide, synergist, herbicide or plant growth regulator, preferably a fungicide.

In a further aspect the invention provides a method comprising treating a seed with abscisic acid and a fungicidally active compound, which fungicidally active compound is a succinate dehydrogenase inhibitor. For example, said treatment will usually result in a seed coated with abscisic acid and the fungicidally active compound. The abscisic acid and fungicidally active compound may be applied to the seed simultaneously, e.g. so that the mixture is homogenous, or they may be applied separately, e.g. to result in layers. In a further aspect the invention provides a seed comprising abscisic acid and a fungicidally active compound, which fungicidally active compound is a succinate dehydrogenase inhibitor.

In a further aspect the invention provides use of abscisic acid for increasing the fungicidal potency of a fungicidally active compound, which fungicidally active compound is a succinate dehydrogenase inhibitor. For example, the use of abscisic is for increasing the fungicidal potency of the fungicidally active compound in a method comprising applying to a useful plant, the locus thereof or propagation material thereof a combination of abscisic acid and a fungicidally active compound.

Preferably the useful plant is one that is at risk of an infection of *Septoria tritici* (*Mycosphaerella graminicola*).

Reference to abscisic acid includes reference to abscisic acid analogues, although preferably refers to abscisic acid per se. Such analogues include and are preferably derivatives of abscisic acid, that may not occur in nature, but which are capable of performing substantially the same function in a plant as natural abscisic acid. Examples of abscisic acid analogues include aryl sulphonamide analogues of abscisic acid e.g. pyrabactin and pyrabactin based-ABA receptor agonists such as those described in Melcher et al., Nature Structural & Molecular Biology, 2010, 17, 1102-1108.

The succinate dehydrogenase inhibitor class of fungicides includes phenyl benzamides, e.g. benodanil, flutolanil and mepronil; pyridinyl-ethyl-benzamides, e.g. fluopyram, furan-carboxamides, e.g. fenfuram, oxathin-carboxamides, e.g. carobxin oxycarboxin; thiazole-carboxamides, e.g. thifluzamide; pyrazole carboxamides, e.g. bixafen, furametpyr, isopyrazem, penflufen, penthiopyrad and sedaxane; and pyridine carboxamides, e.g. boscalid.

Preferably the succinate dehydrogenase inhibitor fungicide according to the invention is a compound of formula I:

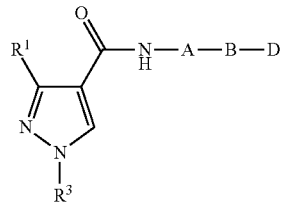
(I)

wherein $R^1$ is $C_1$-$C_4$haloalkyl;
$R^3$ is methyl or ethyl;
A is thienyl, phenyl, or ethylene each optionally substituted by one to three groups independently selected from halogen, methyl and methoxy;
B is a direct bond, cyclopropylene, an annelated bicyclo[2.2.1]heptane- or bicyclo[2.2.1]heptene ring;
D is hydrogen, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ alkylidene, $C_1$-$C_6$ haloalkylidene, phenyl or phenyl optionally substituted by one to three substituents independently selected from halogen and trihalomethylthio.

The compound of formula I is preferably a compound of formula II (Isopyrazam), a compound of formula III (Sedaxane), a compound of formula IV, a compound of formula V (Penthiopyrad), a compound of formula VI (Bixafen), a compound of formula VII (Fluxapyroxad), a compound of formula VIII, or a compound of formula IX:

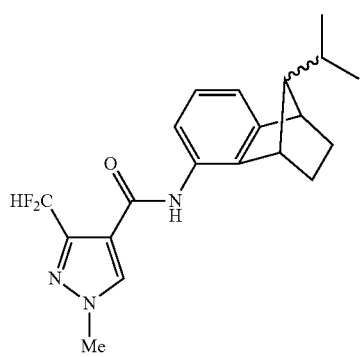
(II)

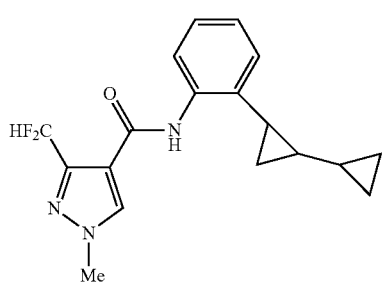
(III)

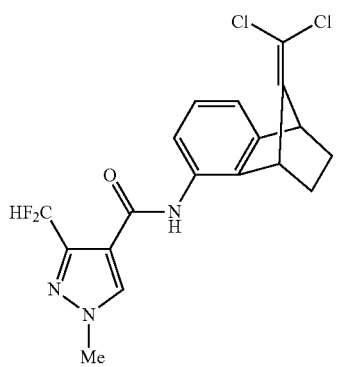
(IV)

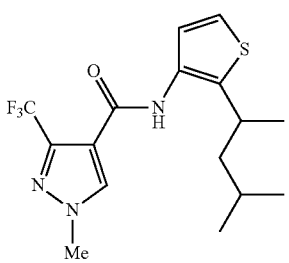
(V)

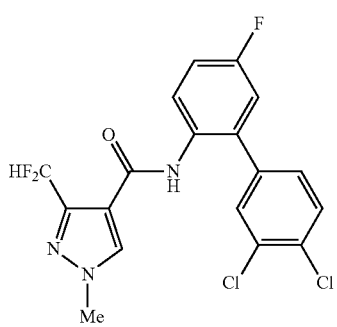
(VI)

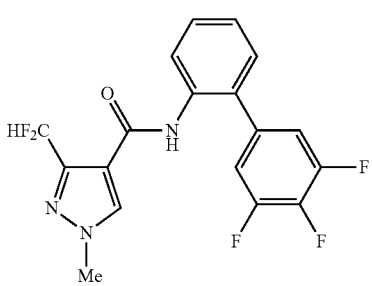
(VII)

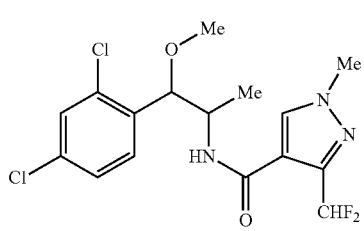
(VIII)

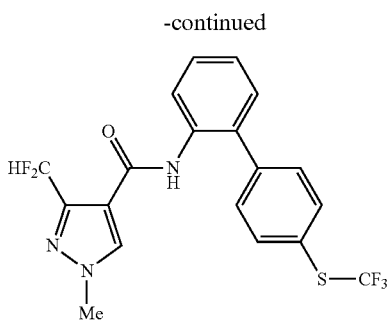
(IX)

Isopyrazam, Sedaxane, Penthiopyrad, Fluxapyroxad and Bixafen are known fungicides. The compound of formula IV is known, e.g. from WO 2007/048556, the compound of formula VIII is known e.g. from WO 2010/000612, the compound of formula IX is known e.g. from WO 2008/053044. Preferably the succinate dehydrogenase inhibitor fungicide is isopyrazam.

An additional active ingredients in the compositions of the invention may be e.g. an insecticide, fungicide, synergist, herbicide or plant growth regulator, preferably a fungicide, for example, one or more of Azoxystrobin (131860-33-8), Dimoxystrobin (149961-52-4), Enestrobin (238410-11-2), Fluoxastrobin (193740-76-0), Kresoxim-methyl (143390-89-0), Metominostrobin (133408-50-1), Orysastrobin (248593-16-0), Picoxystrobin (117428-22-5), Pyraclostrobin (175013-18-0), trifloxystrobin (141517-21-7), Azaconazole (60207-31-0), Bromuconazole (116255-48-2), Cyproconazole (94361-06-5), Diniconazole (83657-24-3), Diniconazole-M (83657-18-5), Epoxiconazole (13385-98-8), Fenbuconazole (114369-43-6), Fluquinconazole (136426-54-5), Flusilazole (85509-19-9), Flutriafol (76674-21-0), Hexaconazole (79983-71-4), Imazalil (58594-72-2), Imibenconazole (86598-92-7), Ipconazole (125225-28-7), Metconazole (125116-23-6), Myclobutanil (88671-89-0), Oxpoconazole (174212-12-5), Pefurazoate (58011-68-0), Penconazole (66246-88-6), Prochloraz (67747-09-5), Propiconazole (60207-90-1), Prothioconazole (178928-70-6), Simeconazole (149508-90-7), Tebuconazole (107534-96-3), Tetraconazole (112281-77-3), Triadimefon (43121-43-3), Triadimenol (55219-65-3), Triflumizole (99387-89-0), Triticonazole (131983-72-7), Diclobutrazol (76738-62-0), Etaconazole (60207-93-4), Fluconazole (86386-73-4), Fluconazole-cis (112839-32-4), Thiabendazole (148-79-8), Quinconazole (103970-75-8), Fenpiclonil (74738-17-3), Fludioxonil (131341-86-1), Cyprodinil (121552-61-2), Mepanipyrim (110235-47-7), Pyrimethanil (53112-28-0), Aldimorph (91315-15-0), Dodemorph (1593-77-7), Fenpropimorph (67564-91-4), Tridemorph (81412-43-3), Fenpropidin (67306-00-7), Spiroxamine (118134-30-8), Isopyrazam (881685-58-1), Sedaxane (874967-67-6), Bixafen (581809-46-3), Penthiopyrad (183675-82-3), Fluxapyroxad (907204-31-3), Boscalid (188425-85-6), Penflufen (494793-67-8), Fluopyram (658066-35-4), Mandipropamid (374726-62-2), Benthiavalicarb (413615-35-7), Dimethomorph (110488-70-5), Chlorothalonil (1897-45-6), Fluazinam (79622-59-6), Dithianon (3347-22-6), Metrafenone (220899-03-6), Tricyclazole (41814-78-2), Mefenoxam (70630-17-0), Metalaxyl (57837-19-1), Acibenzolar (126448-41-7) (Acibenzolar-5-methyl (126448-41-7)), Mancozeb (8018-01-7), Ametoctradine (865318-97-4) Ipconazole (125225-28-7), Amisulbrom (348635-87-0), Cyflufenamid (180409-60-3), Ethaboxam (16650-77-3), Fluopicolide (239110-15-7), Fluthianil (304900-25-2), Isotianil (224049-04-1), Proquinazid (189278-12-4), Valiphenal (283159-90-0), 1-methyl-cyclopropene (3100-04-7), Trifloxystrobin (141517-21-7), Sulfur (7704-34-9), Copper ammoniumcarbonate (CAS 33113-08-5); Copper oleate (CAS 1120-44-1); Folpet (133-07-3), Quinoxyfen (124495-18-7), Captan (133-06-2), Fenhexamid (126833-17-8), Glufosinate and its salts (51276-47-2, 35597-44-5 (S-isomer)), Glyphosate (1071-83-6) and its salts (69254-40-6 (Diammonium), 34494-04-7 (Dimethylammonium), 38641-94-0 (Isopropylammonium), 40465-66-5 (Monoammonium), 70901-20-1 (Potassium), 70393-85-0 (Sesquisodium), 81591-81-3 (Trimesium)), 1,3-Dimethyl-1H-pyrazole-4-carboxylic acid (2-dichloromethylene-3-ethyl-1-methyl-indan-4-yl)-amide, 1,3-Dimethyl-1H-pyrazole-4-carboxylic acid (4'-methylsulfanyl-biphenyl-2-yl)-amide, 1,3-Dimethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, and 3-[5-(4-Chloro-phenyl)-2,3-dimethyl-isoxazolidin-3-yl]-pyridine— where the additional active ingredient is different to the primary active ingredient.

The mixtures and compositions according to the invention are effective especially against phytopathogenic fungi belonging to the following classes:
Fungi imperfecti (e.g. *Alternaria* spp.), Basidiomycetes (e.g. *Corticium* spp., *Ceratobasidium* spp., *Waitea* spp., *Thanatephorus* spp., *Rhizoctonia* spp., *Hemileia* spp., *Puccinia* spp., *Phakopsora* spp., *Ustilago* spp., *Tilletia* spp.), Ascomycetes (e.g. *Venturia* spp., *Blumeria* spp., *Erysiphe* spp., *Podosphaera* spp., *Uncinula* spp., *Monilinia* spp., *Sclerotinia* spp., *Colletotrichum* spp., *Glomerella* spp., *Fusarium* spp., *Gibberella* spp., *Monographella* spp., *Phaeosphaeria* spp., *Mycosphaerella* spp., *Cercospora* spp., *Pyrenophora* spp., *Rhynchosporium* spp., *Magnaporthe* spp., *Gaeumannomyces* spp., *Oculimacula* spp., *Ramularia* spp., *Botryotinia* spp.) and Oomycetes (e.g. *Phytophthora* spp., *Pythium* spp., *Plasmopara* spp., *Peronospora* spp., *Pseudoperonospora* spp., *Bremia* spp). Furthermore, the mixtures and compositions are effective against *Plasmodiophora brassicae*

According to the invention "useful plants" typically comprise the following species of plants: grape vines; cereals, such as wheat, barley, maize, rice, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

Cereals, particularly wheat, rice, maize and barley are of particular interest for the invention, particularly wheat.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names Genuity®, RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The mixtures and compositions of the present invention may also be used in the field of protecting storage goods against attack of fungi. According to the present invention, the term "storage goods" is understood to denote natural substances of vegetable and/or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The compositions according the present invention can prevent disadvantageous effects such as decay, discoloration or mold. Preferably "storage goods" is understood to denote natural substances of vegetable origin and/or their processed forms, more preferably fruits and their processed forms, such as pomes, stone fruits, soft fruits and citrus fruits and their processed forms. In another preferred embodiment of the invention "storage goods" is understood to denote wood.

Therefore a further aspect of the present invention is a method of protecting storage goods, which comprises applying to the storage goods a mixture or composition according to the invention.

The compositions of the present invention may also be used in the field of protecting technical material against attack of fungi. According to the present invention, the term "technical material" includes paper; carpets; constructions; cooling and heating systems; wall-boards; ventilation and air conditioning systems and the like; preferably "technical material" is understood to denote wall-boards. The compositions according the present invention can prevent disadvantageous effects such as decay, discoloration or mold.

The mixtures and compositions according to the invention are particularly effective against powdery mildews; rusts; leafspot species; early blights and molds; especially against *Septoria, Puccinia, Erysiphe, Pyrenophora* and *Tapesia* in cereals; *Phakopsora* in soybeans; *Hemileia* in coffee; *Phragmidium* in roses; *Alternaria* in potatoes, tomatoes and cucurbits; *Sclerotinia* in turf, vegetables, sunflower and oil seed rape; black rot, red fire, powdery mildew, grey mold and dead arm disease in vine; *Botrytis cinerea* in fruits; *Monilinia* spp. in fruits and *Penicillium* spp. in fruits.

The mixtures and compositions according to the invention are furthermore particularly effective against seedborne and soilborne diseases, such as *Alternaria* spp., *Ascochyta* spp., *Botrytis cinerea, Cercospora* spp., *Claviceps purpurea, Cochliobolus sativus, Colletotrichum* spp., *Epicoccum* spp., *Fusarium graminearum, Fusarium moniliforme, Fusarium oxysporum, Fusarium proliferatum, Fusarium solani, Fusarium subglutinans, Gaumannomyces graminis, Helminthosporium* spp., *Microdochium nivale, Phoma* spp., *Pyrenophora graminea, Pyricularia oryzae, Rhizoctonia solani, Rhizoctonia cerealis, Sclerotinia* spp., *Septoria* spp., *Sphacelotheca reilliana, Tilletia* spp., *Typhula incarnata, Urocystis occulta, Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

The mixtures and compositions according to the invention are furthermore particularly effective against post harvest diseases such as *Botrytis cinerea, Colletotrichum musae, Curvularia lunata, Fusarium semitecum, Geotrichum candidum, Monilinia fructicola, Monilinia fructigena, Monilinia laxa, Mucor piriformis, Penicilium italicum, Penicilium solitum, Penicillium digitatum* or *Penicillium expansum* in particular against pathogens of fruits, such as pome fruits, for example apples and pears, stone fruits, for example peaches and plums, citrus, melons, papaya, kiwi, mango, berries, for example strawberries, avocados, pomegranates and bananas, and nuts.

The mixtures and compositions according to the invention are particularly useful for controlling the following diseases on the following crops:

*Alternaria* species in fruit and vegetables; *Ascochyta* species in pulse crops; *Botrytis cinerea* in strawberries, tomatoes, sunflower, pulse crops, vegetables and grapes, such as *Botry-*

*tis cinerea* on grape; *Cercospora arachidicola* in peanuts; *Cochliobolus sativus* in cereals; *Colletotrichum* species in pulse crops; *Erysiphe* species in cereals; such as *Erysiphe graminis* on wheat and *Erysiphe graminis* on barley; *Erysiphe cichoracearum* and *Sphaerotheca fuliginea* in cucurbits; *Fusarium* species in cereals and maize; *Gaumannomyces graminis* in cereals and lawns; *Helminthosporium* species in maize, rice and potatoes; *Hemileia vastatrix* on coffee; *Microdochium* species in wheat and rye; *Mycosphaerella fijiensis* in banana; *Phakopsora* species in soybeans, such as *Phakopsora pachyrizi* in soybeans; *Puccinia* species in cereals, broadleaf crops and perennial plants; such as *Puccinia recondita* on wheat, *Puccinia striiformis* on wheat and *Puccinia recondita* on barley; *Pseudocercosporella* species in cereals, such as *Pseudocercosporella herpotrichoides* in wheat; *Phragmidium mucronatum* in roses; *Podosphaera* species in fruits; *Pyrenophora* species in barley, such as *Pyrenophora teres* on barley; *Pyricularia oryzae* in rice; *Ramularia collo-cygni* in barley; *Rhizoctonia* species in cotton, soybean, cereals, maize, potatoes, rice and lawns, such as *Rhizoctonia solani* on potato, rice, turf and cotton; *Rhynchosporium secalis* on barley, *Rhynchosporium secalis* on rye; *Sclerotinia* species in lawns, lettuce, vegetables and oil seed rape, such as *Sclerotinia sclerotiorum* on oilseed rape and *Sclerotinia homeocarpa* on turf; *Septoria* species in cereals, soybean and vegetables, such as *Septoria tritici* on wheat, *Septoria nodorum* on wheat and *Septoria glycines* on soybean; *Sphacelotheca reilliana* in maize; *Tilletia* species in cereals; *Uncinula necator, Guignardia bidwellii* and *Phomopsis viticola* in vines; *Urocystis occulta* in rye; *Uromyces* species in beans; *Ustilago* species in cereals and maize; *Venturia* species in fruits, such as *Venturia inequalis* on apple; *Monilinia* species on fruits; *Penicillium* species on citrus and apples.

For example, the mixtures and compositions of the invention are useful for controlling oomycete pathogens, in particular Downy mildew (e.g. *Plasmopora viticola, Bremia lactucae, Peronospora parasitica, Peronospora destructor, Pseudoperonospora cubensis*).

*Phytophthora* blight (*Phytophthora capsici*),

Late blight (*Phytophthora infestans*),

Blue Mold (*Peronospora effusa*) e.g. on the following crops:

*Brassica* vegetables (e.g. Broccoli, Brussels sprouts, Cabbage, Cauliflower, Collards, Kale);

Mustard greens (e.g. head and stem subgroup—Cavalo broccolo, Chinese broccoli, Chinese cabbage, Chinese mustard cabbage and kohlrabi)(leafy greens subgroup—broccoli raab, Chinese cabbage, mizuna, mustard spinach, rape greens);

Bulb vegetables (e.g. Dry bulb (garlic, bulb onion, shallot);

Green onion (e.g. leek, green onions, Welch onion);

Cucurbit vegetables (e.g. Cantaloupe, Chayote, Chinese waxgourd, Cucumber, Gourds, Honeydew, *Momordica* spp. (bitter melon and balsam apple), Muskmelon, Pumpkin, Squash, Watermelon, Zucchini);

Grapes;

Leafy vegetables (e.g. Amaranth, Arugula, Cardoon, Celery (Chinese), Celtuce, Chervil, Chrysanthemum (edible-leaved and garland), Corn saladCress (garden and upland), Dandelion, Dock, Endive, Fennel (Florence), Orach, Parsley, Purslane (garden and winter), Radicchio (red chicory), Rhubarb, Lettuce (leaf and head), Spinach (New Zealand and vine), Swiss chard);

Peppers (bell pepper, non-bell pepper, sweet non-bell pepper).

Suitable Vegetables Include:

*Brassica* Vegetables: Broccoli; Chinese broccoli (gai lon); Brussels sprouts; Cabbage; Chinese cabbage (napa); Chinese mustard cabbage (gai choy); Cauliflower; Cavalo broccoli; Kohlrabi. Broccoli rabb; Chinese cabbage; Collards; Kale; Mizuna; Mustard greens; Mustard spinach; Rape greens. Bulb Vegetables: Onion, bulb, Garlic, Shallot, Green Onion: Green onions; Leek; Welch onion. Cucurbits: Cantaloupe; Chayote; Chinese-waxgourd; Field cucumber; Gourds; Honeydew Melons; *Momordica* spp. (bitter melon, balsam apple); Muskmelon; Watermelon; Pumpkin; Squash; Zucchini. Peppers: Field pepper transplants;

For use on peppers to be treated in the greenhouse and immediately transplanted to the field. Bell peppers, Non-bell peppers, Sweet non-bell peppers. Tomatoes: Field Tomato, Tomatillo, Greenhouse Tomatoes (e.g. for use in greenhouse only—not for transplant to the field). Leafy Vegetables: Field lettuce, leaf and head lettuce. Spinach. Greenhouse Lettuce (e.g. for use in greenhouse only—not for transplant to the field).

The use of abscisic acid in combination with succinate dehydrogenase inhibitor, e.g. isopyrazam, can also result in beneficial effects on the plant, e.g. an increase in plant health, particularly when the plant is a cereal e.g. wheat. An increase in plant health includes increased resistance to abiotic stress conditions and/or biotic stress conditions. Abiotic stress refers, for example, to environmental conditions which are not conducive to plant health, in particular high temperature fluctuations, heat, chill, drought, water-logging, high salinity, high UV radiation exposure, organic, inorganic pollution. Biotic stress refers, for example to stress conditions caused by organisms, for example by pests (such as insects, arachnids, nematodes and the like), competing plants (for example weeds), phytopathogenic fungi and other microorganisms such as bacteria and viruses. It has been found that the methods and compositions of the invention are particularly effective when plants are exposed to abiotic stress conditions.

When applied to the useful plants the fungicidally active ingredient is typically applied at a rate of 5 to 2000 g a.i./ha, particularly 10 to 1000 g a.i./ha, e.g. 50, 75, 100 or 200 g a.i./ha, typically in association with 0.5 to 1000 g/ha, preferably 1 to 750 g/ha, more preferably 2.5 to 500 g/ha, more preferably 5 to 300 g/ha, more preferably 7.5 to 200 g/ha of abscisic acid.

In agricultural practice the application rates of the compositions according to the invention depend on the type of effect desired, and typically range from 20 to 4000 g of total composition per hectare.

When the mixtures and compositions according to the invention are used for treating seed, rates of 0.001 to 50 g of a compound of the fungicidally active compound per kg of seed, preferably from 0.01 to 10 g per kg of seed, and 0.0001 to 50 g of the abscisic acid, per kg of seed, preferably from 0.001 to 10 g per kg of seed, e.g. 0.01 to 10 g per kg of seed are generally sufficient.

The mixtures and composition of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such mixtures and compositions may be produced in conventional manner, e.g. by mixing the active ingredients with at least one appropriate inert formulation adjuvant (for example, diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

Customary formulation ingredients are, for example, formulation ingredients that are do not have any significant biological activity, or have no biological activity. They include, for example, diluents, solvents, fillers, surfactants, biocides, anti-freeze, stickers, thickeners and compounds that provide adjuvancy effects.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules. A typical a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation. A typical pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least a compound of the fungicidally active ingredient together with the plant hormone and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Application of the fungicide and abscisic acid, e.g. as a "combination" may be in a single "ready-mix" form, such as a ready-to-use formulation comprising the two components in a fixed ratio; or in a combined spray mixture composed from separate formulations of the single active ingredient components, e.g. a "tank-mix", or in a combined use of the individual ingredients when applied in common spray plan or schedule a sequential manner, i.e. one after the other with a reasonably short period, e.g. a few hours. When applied in separate sprays following each other, the order of applying the components is not essential for achieving the effect according to the present invention.

The Examples which follow serve to illustrate the invention. The invention is not limited to these Examples. All references mentioned herein are incorporated by reference.

EXAMPLE

*Mycosphaerella graminicola* (*Septoria tritici*)/Wheat/Preventative (*Septoria tritici* Leaf Spot on Wheat)

The isopyrazam is formulated as an emulsion concentrate formulation and mixed with water to form a stock solution and ultrasonically agitated in order to achieve homogeneous distribution. Spray solutions are made up from the stock solution by dilution in water/isopropanol (10% isopropanol v/v), with abscisic acid added where needed as a tank mix to the diluted stock solution, and mechanically stirred just before spraying. Foliar application is at 200 L/ha using an application device spraying with a single nozzle (Lechler type) 60 cm above the plants. Typically two-week old wheat plants cv. Riband are sprayed with the spray solution in the spray chamber of the application device. The test plants are inoculated by spraying a spore suspension on them one day after application. After an incubation period of 1 day at typically 22° C./21° C. (day/night) and 95% rh, the inoculated test plants are kept at typically 22° C./21° C. (day/night) and 70% rh in a greenhouse. Percentage efficacy is assessed by direct visual comparison to untreated check plants when an appropriate level of disease appears on the untreated checks (typically 14-19 days after application). The results are shown in Table 1.

TABLE 1

| Isopyrazam (mg/ml) | Abscisic acid (% w/v) | % Disease Control |
|---|---|---|
| — | — | 0 |
| — | 0.0238 | 0 |
| — | 0.0025 | 0 |
| 625.00 | — | 80 |
| 156.25 | — | 67 |
| 39.06 | — | 50 |
| 9.77 | — | 10 |
| 2.44 | — | 3 |
| 595.24 | 0.0238 | 87 |
| 148.81 | 0.0238 | 77 |
| 37.20 | 0.0238 | 77 |
| 9.30 | 0.0238 | 57 |
| 2.32 | 0.0238 | 57 |
| 621.89 | 0.0025 | 87 |
| 155.47 | 0.0025 | 73 |
| 38.87 | 0.0025 | 63 |
| 9.72 | 0.0025 | 47 |
| 2.43 | 0.0025 | 43 |

"% w/v" of Abscisic acid is relative to the spray solution which was sprayed at 200 L/ha. Likewise, "mg/ml" of isopyrazam is relative to the spray solution.

Although all spray solutions were made up and diluted in water/isopropanol (10% isopropanol v/v), this water/isopropanol treatment alone was seen to give zero disease control, thereby confirming isopyrazam and any abscisic acid added to be responsible for any disease control effects seen.

The invention claimed is:

1. A method comprising applying to a useful plant, the locus thereof or propagation material thereof a combination of abscisic acid and isopyrazam, and wherein the combination exhibits an increase in fungicidal activity as compared to isopyrazam without abscisic acid.

2. A method according to claim 1, wherein the useful plant is at risk of an infection of *Septoria tritici* (*Mycosphaerella graminicola*).

3. A method according to claim 1, wherein the useful plant is a cereal.

4. A method according to claim 1, wherein the useful plant is wheat.

5. A method of increasing the fungicidal activity of isopyrazam, the method comprising applying a combination of abscisic acid and isopyrazam to a useful plant, the locus thereof or propagation material thereof, and wherein the combination exhibits an increase in fungicidal activity as compared to isopyrazam without abscisic acid.

6. A composition comprising abscisic acid and isopyrazam wherein the composition, when in contact with a fungal pathogen, exhibits an increase in fungicidal activity as compared to isopyrazam without abscisic acid.

7. A composition according to claim 6, comprising a further active ingredient.

8. A seed comprising a combination of abscisic acid and isopyrazam, wherein the combination, when in contact with a fungal pathogen, exhibits an increase in fungicidal activity as compared to isopyrazam without abscisic acid.

* * * * *